US00PP30126P3

(12) United States Plant Patent
Ledbetter

(10) Patent No.: US PP30,126 P3
(45) Date of Patent: Jan. 22, 2019

(54) GRAVEVINE NAMED 'SOLBRIO'

(50) Latin Name: ***Vitis vinifera* L.**
Varietal Denomination: Solbrio

(71) Applicant: The United States of America, as Represented by the Secretary of Agriculture, Washington, DC (US)

(72) Inventor: Craig A. Ledbetter, Clovis, CA (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/731,420

(22) Filed: Jun. 6, 2017

(65) Prior Publication Data

US 2018/0352695 P1 Dec. 6, 2018

(51) Int. Cl.
*A01H 5/08* (2018.01)

(52) U.S. Cl.
USPC ..... Plt./205

(58) Field of Classification Search
USPC ..... Plt./205
CPC ..... A01H 5/08; A01H 5/0812; A01H 6/88; A01H 5/00; A01H 5/02
See application file for complete search history.

(56) References Cited

PUBLICATIONS

UC IPM Identification:Characteristics of Broadleaves Leaf shape 2016, retrieved on May 3, 2018, retrieved from the Internet at http://ipm.ucanr.edu/PMG/WEEDS/ID/broadshps.html, one page. (Year: 2016).*

* cited by examiner

*Primary Examiner* — June Hwu
(74) *Attorney, Agent, or Firm* — John Fado; Ariel Atkinson

(57) ABSTRACT

A new and distinct variety of table grape (*Vitis vinifera* L.) named 'Solbrio', particularly characterized by its black skin color of crisp textured and naturally large sized berries; consistent fruit production on spur-pruned vines; and maturing during late July in California's Central San Joaquin Valley.

7 Drawing Sheets

Latin name of genus and species of the plant claimed: 'Solbrio' is a new grapevine plant that is *Vitis vinifera* L.

Variety denomination: The new grapevine plant claimed is of the cultivar denomination 'Solbrio'.

BACKGROUND OF THE INVENTION

The present invention relates to a new and distinct variety of table grape (*Vitis vinifera* L.) known as *Vitis vinifera* L. and herein referred to as 'Solbrio', as herein described and illustrated.

'Solbrio' is particularly characterized by its black skin color of crisp textured and naturally large sized berries; consistent fruit production on spur-pruned vines; and maturing during late July in California's Central San Joaquin Valley.

The new cultivar is a result of a controlled pollination, conducted by the inventor in Parlier, Calif. The objective of the planned hybridization was to develop a new *V. vinifera* cultivar having a desirable combination of characteristics that would facilitate the cultivation of the table grape for producers and satisfy consumers with fruit of high eating quality such as firm, crisp flesh and sweet neutral flavor.

The new and distinct variety of grape plant originated from a hand-pollinated cross of ARS selection B55-70 (non-patented) x ARS selection C49-3 (non-patented) made in 2004 in Parlier, Calif. B55-70 is a black-skinned seedless grape selection with average skin thickness, flesh firmness and berry size that typically ripens in mid-September in the Central San Joaquin Valley. It has a noticeable seed trace, making it suitable as a seed parent for seedless×seedless ovule culture. The pollen parent, C49-3, is characterized as having black skin with a large berry size, firm flesh, and a very small seed trace. C49-3 typically ripens a week prior to B55-70. Both parents of 'Solbrio' are hybrids of the grape genus and species *Vitis vinifera* L. Immature seed resulting from the controlled hybridization of B55-70 x C49-3 were harvested approximately six weeks after pollination and established in vitro, eventually germinating in the laboratory during the fall of 2004. Resulting seedlings were planted in the spring of 2005 in Parlier, Calif. Seedlings from the controlled hybridization began fruiting during the summer of 2006 and one, designated 'Solbrio', was identified for its early ripening attractive black seedless fruit with firm, crisp flesh and neutral flavor, and selected for propagation and evaluation.

During 2007, the original selected plant 'Solbrio' was propagated asexually by rooting hardwood cuttings during the dormant period and a test plot of 27 vines was established in the Parlier, Calif. vineyard. All asexually propagated plants of 'Solbrio' have been observed to grow true to type after propagation, in both vegetative and fruiting characteristics, as compared with the original selected mother vine.

SUMMARY OF THE INVENTION

The following combination of traits have been observed annually on fruiting 'Solbrio' vines and are determined to be unique characteristics of 'Solbrio', distinguishing it as a new and distinct cultivar: 1. Consistent and productive bearer of large-sized berries without the use of gibberellic acid bloom or sizing sprays. 2. Early-season fruit harvest, typically during the last week of July, in the Central San Joaquin Valley of Calif. 3. Consistent and productive bearer of fruit from spur-pruned vines. 4. Mature berries having an attractive black skin with crisp and crunchy flesh texture and a sweet neutral flavor.

BRIEF DESCRIPTION OF THE PHOTOGRAPHS

The accompanying photographs illustrate the overall appearance of the new 'Solbrio' table grape cultivar at nine years of age, showing the colors as true as is reasonably possible with colored reproductions of this type. Colors in the photos may differ slightly from the color values cited in the detailed botanical description, which accurately describe the color of 'Solbrio'. The colors shown are as true as can be reasonably obtained by conventional photographic procedure.

FIG. 1 shows dormant mature canes of 'Solbrio' with their natural coloration. The smooth surface texture of the mature canes is also evident.

FIG. 2 shows the lower half of a 'Solbrio' trunk. Natural coloration of the trunk bark, both undisturbed and sun-bleached as well as after having the shaggy bark stripped from the trunk, are evident in the figure FIG. 3 depicts the curvature in young shoot tips of 'Solbrio'. Also evident from this figure are the glabrous upper surfaces of young leaves and the red streaking of young stem internodes and tendril tips on sun exposed surfaces.

DETAILED DESCRIPTION OF THE INVENTION

Figure 1:
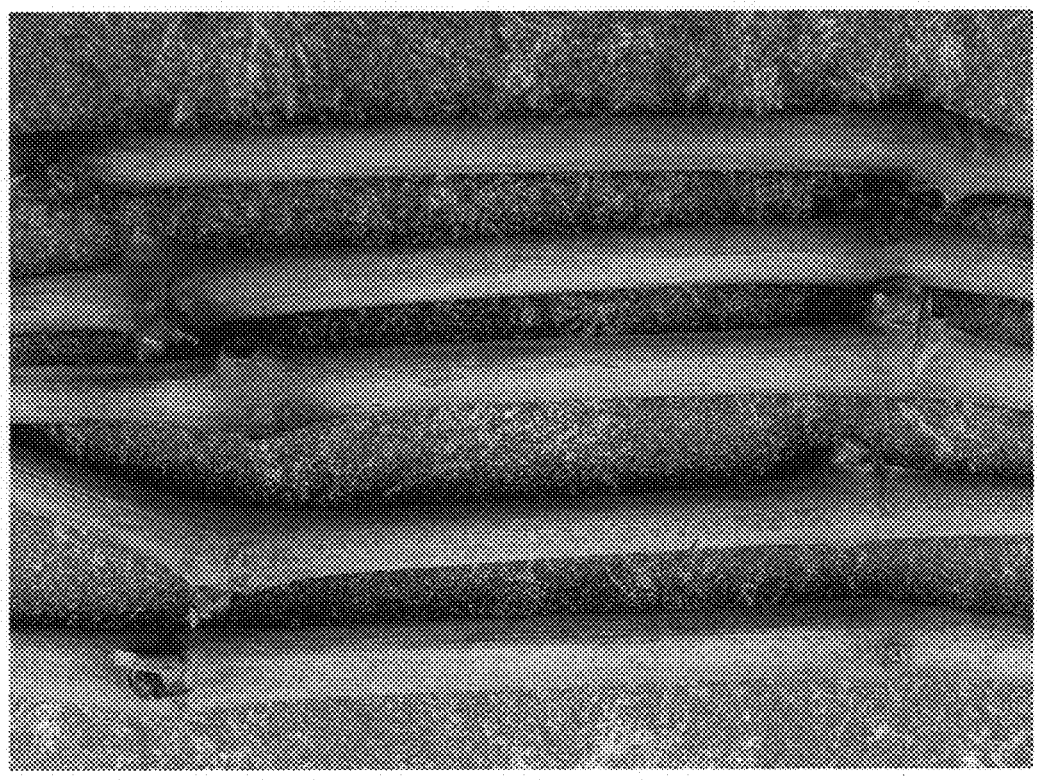

The new 'Solbrio' grapevine has not been observed growing under all possible environmental conditions. The phenotype of the new cultivar may vary with variations in environment (temperature extremes, degree hour accumulation, light intensity and availability, soil type & fertility) without any genotypic changes in the grapevine.

The previously mentioned figures along with the following measured characters describe the vegetative and reproductive organs of 'Solbrio' as grown in Parlier, Calif. under cultural conditions closely approximating those generally used in commercial table grape production. The description is believed to apply to vines of the new 'Solbrio' cultivar grown under similar conditions of soil and climate elsewhere. However, measurements of any individual vine or group of vines of the new 'Solbrio' cultivar may vary from the stated averages.

In a comparison with parental accessions B55-70 (seed parent) and C49-3 (pollen parent), the new cultivar 'Solbrio' differs primarily in the characters listed below in Table 1:

TABLE 1

| CHARACTER | SEED PARENT B55-70 | NEW CULTIVAR Solbrio | POLLEN PARENT C49-3 |
|---|---|---|---|
| RIPENING TIME | Mid September | Late July | Early September |
| SEED TRACE SIZE | Detectable | Non-detectable | Non-detectable |
| EATING QUALITY | Average | Very good | Average |
| FRUITFULNESS | Average | High | Average |
| PEDICLE THICKNESS | Average | Average | Robust |

Of the many commercial table grape cultivars known to the inventor, the most similar in comparison to the new cultivar 'Solbrio' is 'Summer Royal'. The new cultivar 'Solbrio' is compared with 'Summer Royal' using UPOV descriptors for the nine phenological, vegetative and fruit characters listed below in Table 2.

TABLE 2

| UPOV CHARACTER | UPOV CODE | NEW CULTIVAR Solbrio | COMMERCIAL CULTIVAR Summer Royal |
|---|---|---|---|
| TIME OF BUD BURST | 1 | Early* | Medium |
| SHOOT: LENGTH OF TENDRIL | 17 | Very long | Long |
| MATURE LEAF: PROFILE IN CROSS SECTION | 21 | Flat | V-shaped |
| MATURE LEAF: DEPTH OF UPPER LATERAL SINUSES | 24 | Very shallow | Medium |
| MATURE LEAF: SHAPE OF UPPER LATERAL SINUSES | 25 | Open | Slightly overlapped |
| ANTHOCYANIN COLORATION OF MAIN VEINS ON MATURE LEAF UPPER SURFACE | 31 | Absent | Very strong |
| BUNCH: SIZE | 36 | Medium | Large |
| BUNCH: LENGTH OF PEDUNCLE | 38 | Short | Medium |
| BERRY SHAPE | 40 | Elliptic | Circular |

*Descriptors of UPOV characters for 'Solbrio' and 'Summer Royal' as referenced in 'Guidelines for the conduct of tests for distinctness, uniformity and stability. Grapevine (*Vitis L.*)' TG/50/8, Grapevine, 1999 Mar. 24.

Morphological details of the new 'Solbrio' table grape cultivar were collected during the 2015 and 2016 growing seasons when vines were eight and nine years old, respectively. Evaluated vines were grown on their own roots. Twenty-seven own rooted vines of 'Solbrio' were available for collection of data for the detailed description presented below. Color code designations are provided by reference to Dictionary of Color, A. Maerz and M. R. Paul, McGraw-Hill Book Company, Inc., (1930). This description is in accordance with UPOV terminology. Color designations, color descriptions and other phenotypical descriptions may deviate from the stated values and descriptions depending upon variation in environmental, seasonal, climatic and cultural conditions.

Mature canes:

*Size*.—Diameter — Mature dormant canes — Medium diameter, medium vigor, semi-drooping in growth habit.

*Mature canes*.—Diameter — Internode Base — approximately 10.7 mm.

*Mature canes*.—Diameter — Internode Midpoint — approximately 9.0 mm.

*Mature canes*.—Diameter — Internode Tip — approximately 3.8 mm.

*Mature canes*.—Diameter — Node Base — approximately 12.7 mm.

*Mature canes*.—Diameter — Node Midpoint — approximately 10.8 mm.

*Mature canes*.—Diameter — Node Tip — approximately 5.6 mm.

*Internode length*.—Base — Approximately 7.3 cm.

*Internode length*.—Midpoint — Approximately 11.0 cm.

*Internode length*.—Tip — Approximately 5.9 cm.

*Average length of canes*.—Approximately 338 cm, range 241 cm-487 cm.

*Average number of nodes/cane*.—Approximately 41, range 30-61.

*Surface texture*.—Smooth. (FIG. 1).

*Color of mature cane*.—Plate 14 C8 (Mocha bisque).

*Shape of mature cane*.—Round.

Dormant buds:

*Bud color*.—Plate 15 C11 (Cocoa brown).

*Bud texture*.—Smooth.

*Dormant bud* (*compound bud or eye*).—Width — At base of cane approximately 5.0 mm; at midpoint of cane approximately 5.8 mm and at tip of cane approximately 4.4 mm. The average number of buds on a current, single-season growth cane is approximately 41.

*Date of bud break*.—Approximately 1 Mar. 2016.

Vine:

*Size*.—Medium. Grapevine size was determined on grapevines growing on a three cross arm 'T' trellis with the top cross arm approximately 122 cm long, being set approximately 193 cm above the ground; the middle cross arm approximately 107 cm long, being set approximately 161 cm above the ground; and the lower cross arm approximately 91 cm long, being set approximately 128 cm above the ground.

Trunk:

*Size*.—Medium.

*Size*.—Height — Approximately 103 cm above the soil surface, ranging from 79-124 cm.

*Size*.—Trunk cross sectional area — Approximately 82.1 $cm^2$ (ranging from 46-118 $cm^2$) as measured at 66 cm above the soil surface.

Figure 2:
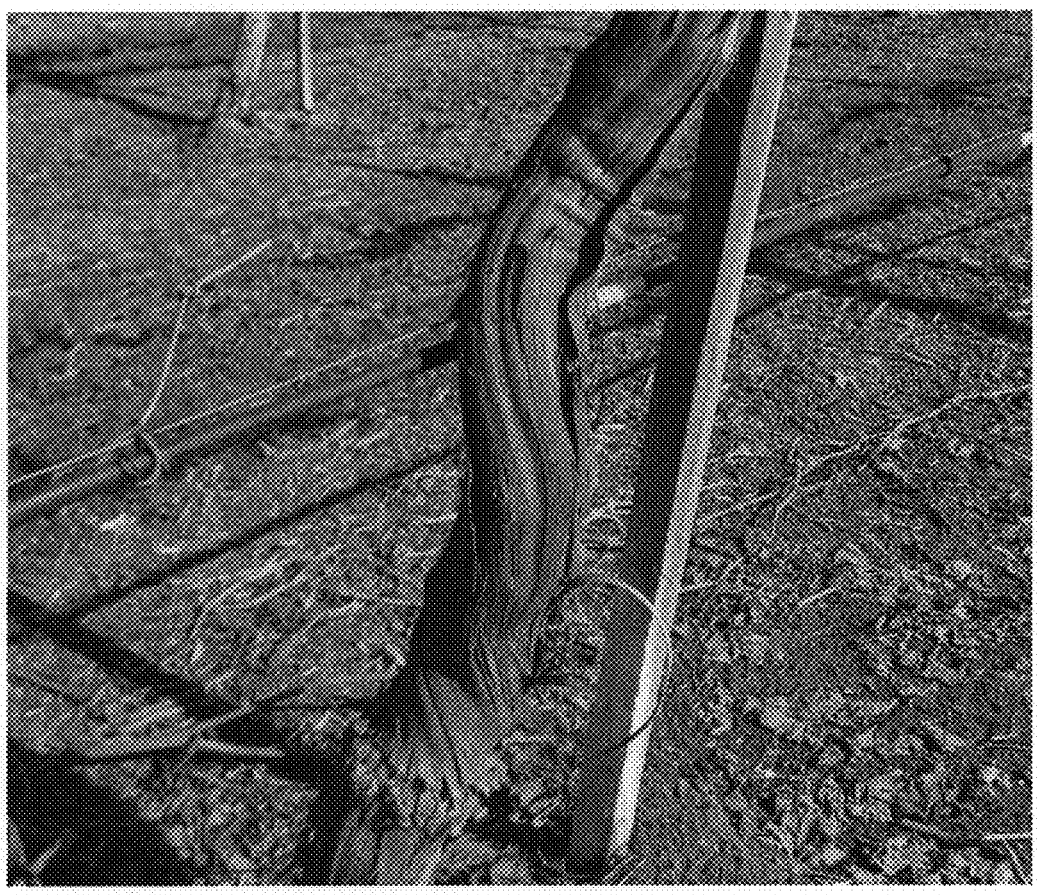

*Bark*.—Color — Undisturbed appearance after sun-bleaching in the vineyard. Plate 56 E3. Appearance after shaggy sun-bleached bark has been stripped from trunk. Plate 7 A11 (Vandyke Brown) (FIG. 2).

Shoots:

*Young shoot tips*.—Unopened meristematic leaves are covered with white felty indument. Red coloration (Plate 7 J4) is evident in teeth on young leaf margins and in young tendril tips.

*Diameter of young shoots in spring*.—(Measured when shoot length is approximately 10-14 inches). At base approximately 6.4 mm, at midpoint approximately 5.5 mm and at tip approximately 3.2 mm.

*Internode length*.—Approximately 6.5 cm at $4^{th}$ internode from base.

*Young shoots*.—Color. Plate 21 L8 with slight red streaking on sun exposed side.

Figure 3:
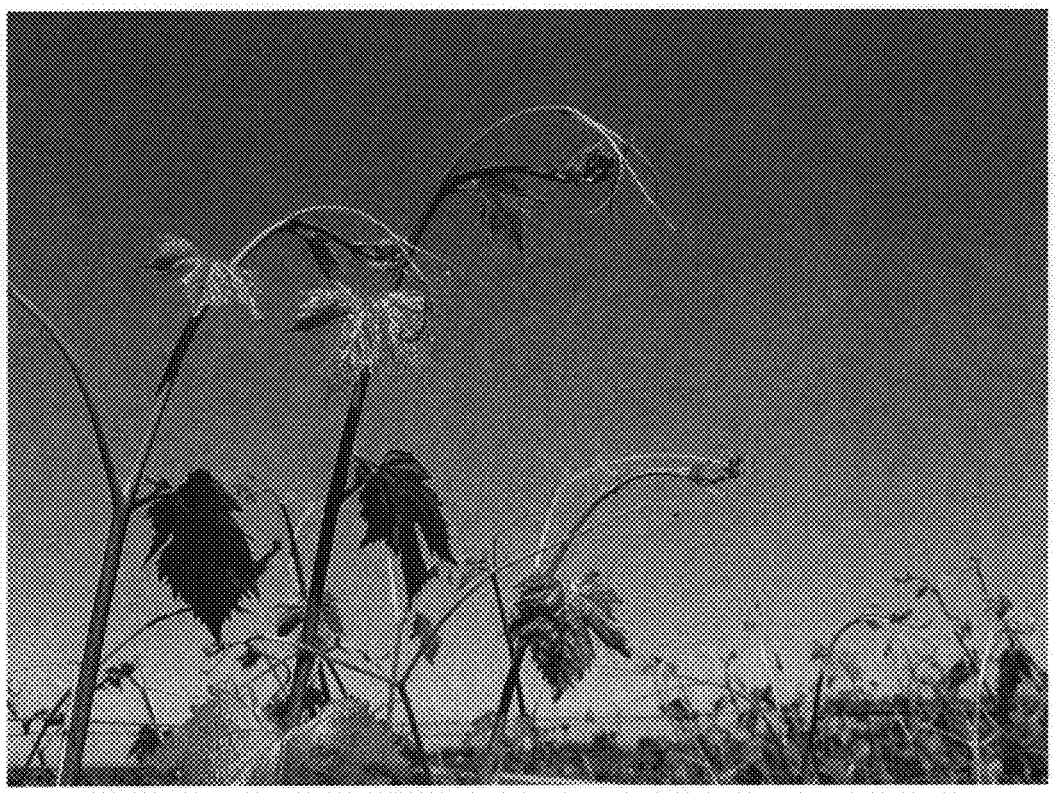

*Interstem of shoot tip*.—Color Plate 20 L9 (Eden Green) with slight red streaking on sun exposed side (FIG. 3).

*Shoot shape*.—Generally slightly curved at tip.

*Shoot tip*.—Form Fully open.

Leaves:

*Mature*.—

*Size*.—Leaves simple and alternate. The mid vein (L1) is approximately 15.5 cm long, vein L2 is approximately 12.4 cm long and vein L3 is approximately 8.2 cm long. The angles between leaf veins are as follows: L1/L2 is approximately 40 degrees, L1/L3 is approximately 82 degrees and L1/$1^{st}$ vein departing from L3 is approximately 124 degrees.

*Average blade length*.—Approximately 15.5 cm.

*Average blade width*.—Approximately 16.5 cm.

Figure 4:
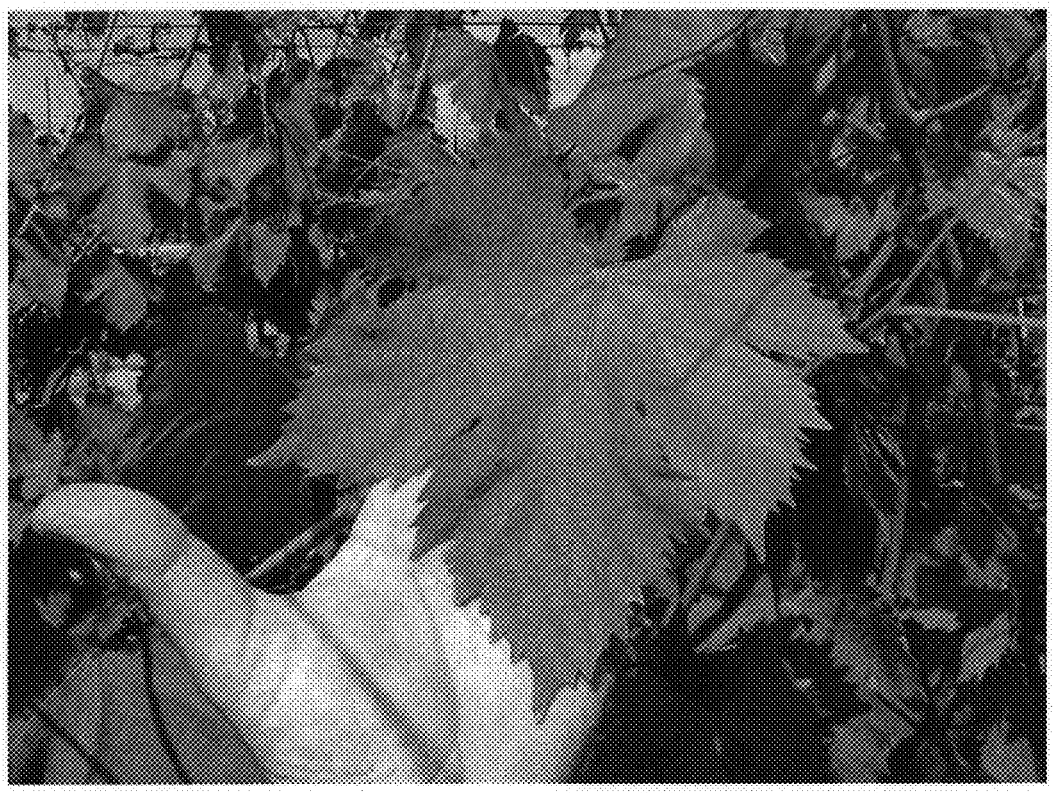
FIG. 4 shows the general cuneiform 5-lobe leaf shape of a 'Solbrio' mature leaf. Also evident from this figure are the glabrous upper leaf surface, the Lyre-shaped half open petiole sinus and the serrated leaf margin having both sides strait and both sides convex.

*Shape*.—Cuneiform (FIG. 4).

*Lobe number*.—Approximately 5.

*Color*.—Upper surface Plate 23 E11 (Monticello Green) Upper surface is glabrous and generally smooth.

*Color*.—Lower surface Plate 21 L8. Lower surface is glabrous with few short erect hairs on sides of leaf veins at junction of petiole and leaf blade.

*Leaf vein*.—Color (as apparent on lower leaf surface) Plate 18 H4. No red pigmentation on veins of leaf.

*Leaf vein*.—Thickness L1 vein thickness at center of leaf is approximately 1.74 mm

*Leaf margin*.—Serrated with teeth shape being a mixture of both sides strait and both sides convex. Mature leaf teeth are generally short to medium in length.

*Petiole sinus*.—Lyre shaped and half open. On mature leaves, sinus depth is approximately 3.7 cm and 3.6 cm at its widest point.

*Petiole size*.—Medium.

*Petiole diameter*.—Approximately 3.1 mm.

*Petiole length*.—Approximately 12.2 cm.

*Petiole color*.—Plate 18 L8 (Eve green).

Young leaves:

*Color*.—Upper surface Plate 14 L1 (Palmleaf) Upper surface is glabrous.

*Color*.—Lower surface Plate 23 L3 (Hellebore Green) Lower surface is glabrous with few short erect hairs on sides of leaf veins at junction of petiole and leaf blade.

*Shape unfolded*.—Concave.

*Petiole*.—Color Plate 20 L7 with slight red striping along length of petiole.

*Stipules*.—Paper-like and diminutive.

Tendrils:

*Tendril size*.—Length — approximately 28.4 cm.

*Tendril size*.—Diameter — as measured just distil of first fork juncture of tendril, approximately 2.41 mm.

*Tendril shape*.—Usually trifurcated and curled on distil ends.

*Tendril pattern*.—Beginning with first tendrils found on nodes 7 and 8, followed by tendrils occurring on nodes 10, 11, 13, 14, 16, 17, with this intermittent pattern repeating to the distil end of the cane.

*Young tendril color*.—Plate 19 L6 (Calliste Green).

Flowers:

*Flower size*.—Medium.

*Unopened flower*.—Length — Approximately 3.44 mm.

*Unopened flower*.—Diameter — Approximately 1.91 mm.

*Unopened flower*.—Surface texture — smooth.

*Date of bloom*.—First bloom — About 20 Apr. 2016.

*Date of bloom*.—Full bloom — About 28 Apr. 2016 at 80%.

*Inflorescence*.—Panicle.

*Cluster size*.—During bloom — generally medium.

*Cluster length*.—Approximately 12.8 cm.

*Cluster width*.—Approximately 5.9 cm.

*Peduncle length*.—Approximately 4.4 cm.

*Peduncle diameter*.—The immature peduncle is not round, but is essentially angular, creating two distinct sides. Small side diameter is approximately 3.09 mm, large side diameter is approximately 4.12 mm and the large side: small side diameter ratio is approximately 1.33.

*Shape of cluster*.—Generally conical.

*Calyptra color*.—Plate 19 K8.

*Sex*.—Hermaphroditic.

*Stamens*.—Five per flower and erect.

*Ovary color*.—Plate 20 J11.

*Pollen*.—Normal, fertile, abundant.

*Anthers*.—Color — Plate 10 I1 (Reed Yellow).

Figure 5:
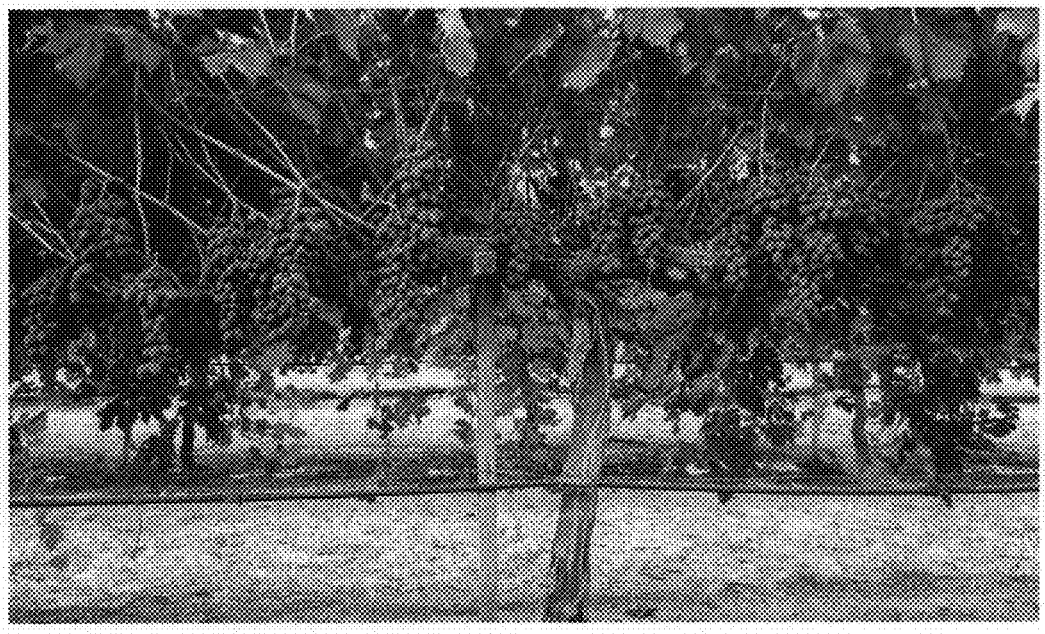
FIG. 5 shows the typical crop load for 'Solbrio' from a spur pruned vine. Evident in this figure are the abundant bloom present on 'Solbrio' berries and the trunk color after shaggy bark has been removed.

Fruit:

*Maturity when described*.—Ripe for commercial harvesting and shipment approximately third week of July in Parlier, Calif. (FIG. 5).

*Cluster size*.—Spur pruned vines, approximately 408 g.

*Cluster length*.—Approximately 20.5 cm.

*Cluster width*.—Approximately 11.1 cm.

Figure 6:
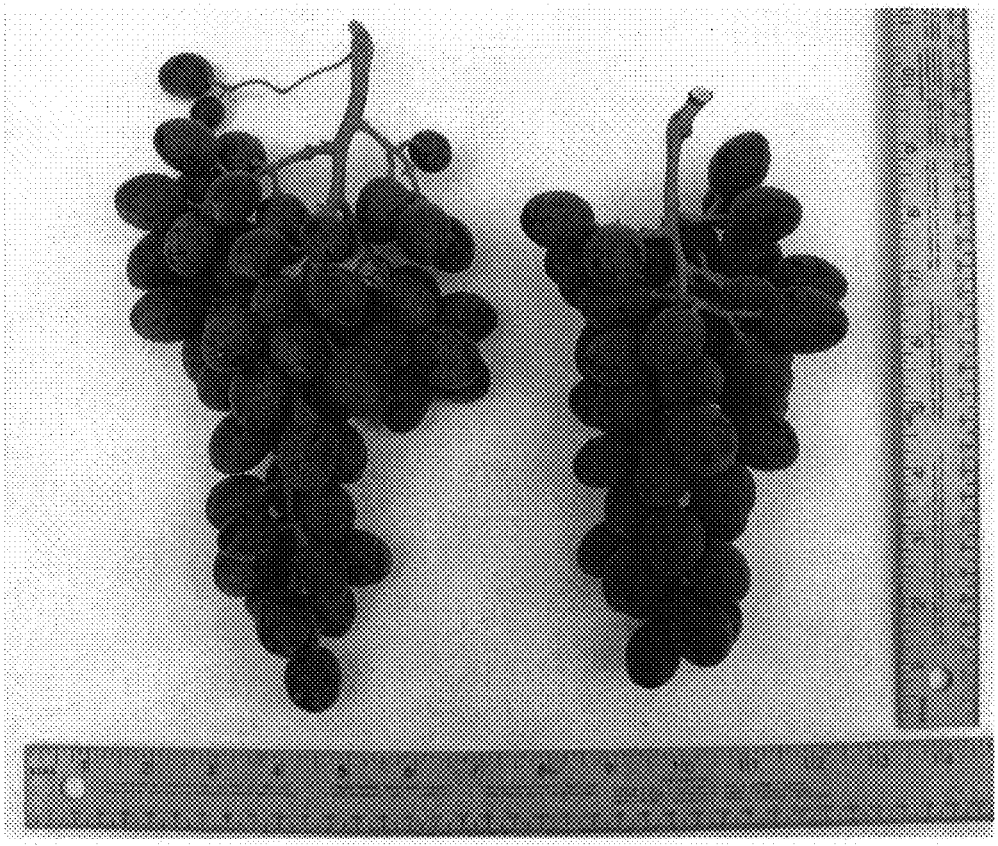
FIG. 6 shows the general conical shape of 'Solbrio' fruit clusters. Also evident in this figure are the medium berry density of mature fruit clusters, the smooth and glabrous texture of the peduncle and the abundant bloom present on the elliptic berries.

*Cluster shape*.—Generally conical, occasionally with a wing (FIG. 6).

*Cluster density*.—Medium density, on average clusters have 60 berries per cluster.

*Clusters per vine*.—Approximately 59, spur pruned vines.

*Clusters per shoot*.—Approximately 2.1 clusters per shoot, spur pruned vines.

Peduncle:

*Size*.—Length Approximately 3.95 cm.

*Size*.—Diameter Approximately 4.79 mm.

*Color*.—Plate 19 L7.

*Texture*.—Smooth and glabrous.

Pedicel: Good attachment between berry and pedicel.

*Size*.—Length Approximately 9.2 mm.

*Size*.—Diameter Approximately 2.2 mm.

*Color*.—Plate 19 L5 (Cosse green).

*Texture*.—Glabrous, somewhat bumpy surface with a few brown lenticels.

*Brush*.—Length Approximately 3.18 mm.

*Brush*.—Color Plate 55 L8 (Rubient).

Berry:

*Size*.—Large, approximately 8.1 g.

Figure 7:
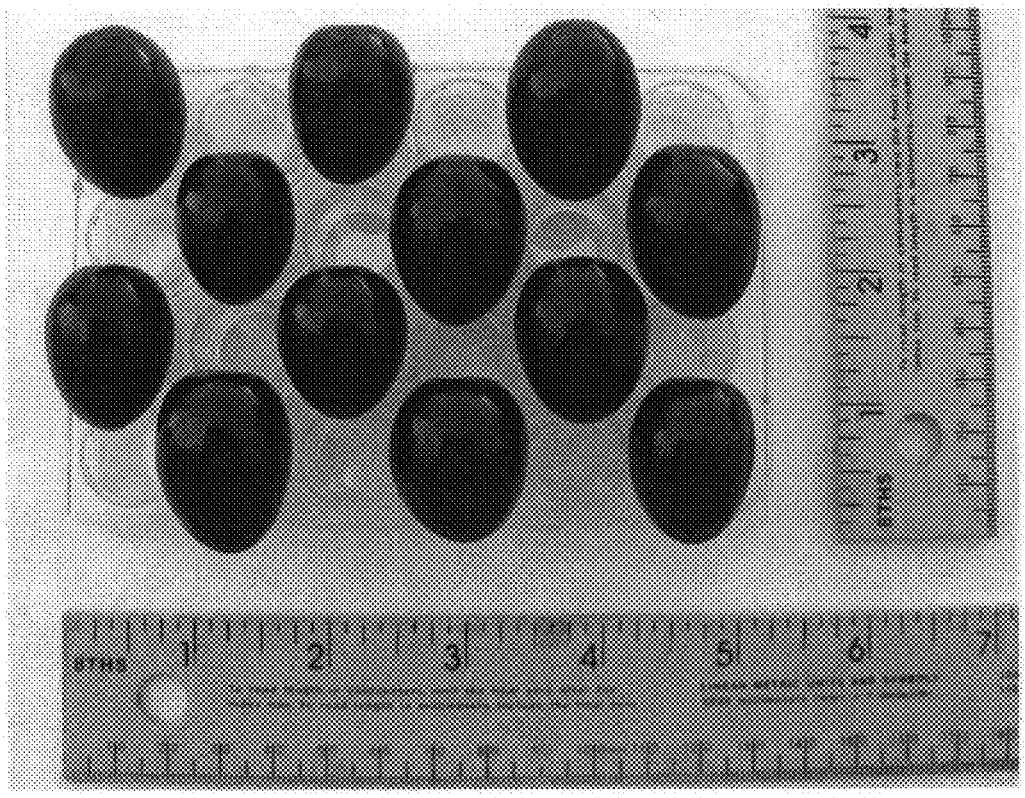
FIG. 7 shows 12 berries of 'Solbrio' in profile. Evident from this figure is the smooth surface texture of the elliptic shaped berries with the bloom removed.

*Shape*.—Elliptic (FIG. 7).

*Length*.—Approximately 2.97 cm.

*Diameter*.—Approximately 2.19 cm.

*Color*.—Plate 40, E3 bloom removed from skin.

*Bloom*.—Abundant.

Skin: Skin adheres well to the berry flesh.

*Thickness*.—Medium thickness.

*Texture*.—Smooth.

*Tendency to crack*.—None.

Flesh:

*Texture*.—Crisp and crunchy.

*Juice production*.—Moderate.

*Color of flesh*.—Generally translucent, Plate 45, A6, with traces of anthocyanin coloration, Plate 47, L7, along central floral axis and beneath berry skin.

*Color of juice*.—Clear.

*Flavor*.—Sweet and neutral flavor.

*Soluble solids*.—Approximately 18.4%.

*Titratable acidity*.—Approximately 0.47 g/100 ml juice.

*Aroma*.—None.

*Ripening*.—Uniform ripening throughout clusters.

*Eating quality*.—Very good.

Disease resistance: Susceptible to powdery mildew. Fungicides were applied to evaluated grapevines to control powdery mildew.

Insect resistance: No known resistances to insects. Evaluated grapevines were treated with insecticides to control leafhoppers.

Resistance to heat/cold: New cultivar 'Solbrio' has only been tested in the central San Joaquin Valley where it performs well. Its performance is unknown when cultured in early regions where it is exposed to high heat. Similarly, the cold hardiness of 'Solbrio' has not been evaluated.

Character of seeds: Stenospermocarpic seedless berries, averaging 1.4 small aborted seed traces per berry which are not noticeable when eaten. When present, average seed trace size is approximately 2.6 mg mass, 3.2 mm in length and 1.6 mm in width. Seed trace color is Plate 47 J4.

Use: Fresh market table grape. New cultivar 'Solbrio' has not been evaluated for wine or raisin qualities.

Keeping quality: Very good.

Shipping and handling qualities: Harvested clusters ship and handle well with very little berry shatter.

Although the new cultivar 'Solbrio' possesses the described characters noted above as a result of growing conditions prevailing in Parlier, Calif. in the Central San Joaquin Valley of Calif., it is to be understood that the characteristics described above are subject to variations of the usual magnitude based on growing conditions, vine training, irrigation and fertilization, pruning, pest control and climatic variation.

We claim:

1. A new and distinct cultivar of grapevine substantially as illustrated and described, characterized by its consistent and productive bearing of large-sized berries without the use of gibberellic acid bloom or sizing sprays, early-season fruit harvest, its consistent and productive bearing of fruit from spur-pruned vines and its mature berries having an attractive black skin with crisp and crunchy flesh texture and a sweet neutral flavor.

* * * * *